US008541167B2

(12) United States Patent
Buller (10) Patent No.: US 8,541,167 B2
(45) Date of Patent: Sep. 24, 2013

(54) METHODS AND COMPOSITIONS FOR VACCINATION

(75) Inventor: Robert Mark Buller, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 927 days.

(21) Appl. No.: 11/569,963

(22) PCT Filed: May 26, 2005

(86) PCT No.: PCT/US2005/018682
§ 371 (c)(1),
(2), (4) Date: Oct. 6, 2008

(87) PCT Pub. No.: WO2005/121378
PCT Pub. Date: Dec. 22, 2005

(65) Prior Publication Data
US 2009/0087451 A1    Apr. 2, 2009

Related U.S. Application Data

(60) Provisional application No. 60/576,840, filed on Jun. 3, 2004.

(51) Int. Cl.
*C12Q 1/70* (2006.01)
*A61K 39/275* (2006.01)

(52) U.S. Cl.
USPC .......................................... 435/5; 424/232.1

(58) Field of Classification Search
None
See application file for complete search history.

(56) References Cited

U.S. PATENT DOCUMENTS 5,886,179 A    3/1999    Arimilli et al.

FOREIGN PATENT DOCUMENTS

WO    00/41463 A2    7/2000
WO    WO 00/41463    *    7/2000

OTHER PUBLICATIONS

Foster, et al. Entecavir Therapy Combined with DNA Vaccination for Persistent Duck Hepatitis B Virus Infection. Antimicrobial Agents and Chemotherapy, 2003;. 47(8):2624-2635.*
Smee et al. Effects of four antiviral substances on lethal vaccinia virus (IHD strain) respiratory infections in mice. International Journal of Antimicrobial Agents. May 2004. vol. 23, pp. 430-437, see entire document.*
Weiner DB, RC Kennedy. Genetic Vaccines. Scientific American, Jul. 1999; vol. 281, Issue 1, p. 50, copyright by Scientific American Inc.
Gurunathan S, DM Klinman, RA Seder. DNA vaccines: Immunology, Application and Optimization, Annual Review of Immunology. 2000; vol. 18: pp. 927-974.
Fedson D, Musher D, Eskola J. Pneumococcal vaccine. In: Vaccines, 3rd ed. Plotkin S, Orenstein W, editors. Philadelphia: WB Saunders Company; 1999: Chapter 22, pp. 553-591.
Andre FE, WJ Stanbury, DE Teuwen. Conventional and New Generation Combined Vaccines. In: Modern Vaccinology. Kurstak E, editor. New York: Plenum Publishing Corporation; 1994.
Chatfield SN, G Dougan, M Roberts. Progress in the Development of Multivalent Oral Vaccines Based on Live Attenuated Salmonella. In: Modern Vaccinology. Kurstak E, editor. New York: Plenum Publishing Corporation; 1994.
Aguado MT, PH Lamber. Controlled release vaccines—biodegradable polylactide/ polyglycolide microspheres as antigen vehicles. Immunobiology 1984; pp. 113-125.
DeClercq E. Therapeautic potential of Cidofovir (HPMPC, Vistide) for the treatment of DNA virus (i.e. herpes-, papova-, pox- and adnovirus) infections. Verhandelingen—Koninklijke Academie voor Geneeskunde van Belgie. 1996; vol. 58, No. I: pp. 19-47, published by Paleiss Der Academein, Brussels.
Cono et al., Smallpox Vaccination and Adverse Reactions. Guidance for Clinicians, Morbidity and Mortality Weekly Report. Feb. 21, 2003. vol. 52, No. RR-4, pp. 1-28.
Smee et al. Effects of four antiviral substances on lethal vaccinia virus (IHD strain) respiratory infections in mice. International Journal of Antimicrobial Agents. May 2004. vol. 23, pp. 430-437, copyright by Elsevier B.V.
Henderson DA, TV Inglesby, JG Bartlett, MS Ascher, E Eitzen, PB Jahrling et al. Smallpox as a biological weapon: medical and public health matangement. Working Group on Civilian Biodefense. JAMA Jun. 9, 1999; vol. 281, No. 22: pp. 2127-2137, copyright by American Medical Association.
Johnson JA, JD Gangemi. Selective inhibition of human papillomavirus ijnduced cell proliferation by (S)-I-[3-hydroxy-2-(phosphonylmethoxy)propyl]cytosine. Antimicrobial Agents and Chemotherapy. 1999; vol. 43, No. 5: pp. 1198-1205, copyright by American Society for Microbiology.
World Health Organzation. The global eradication of smallpox: final report of the Global Commission for the Certification of Smallpox Eradication, Geneva, Dec. 1979. Geneva: World Health Organization, 1980, copyright by World Health Organization, Switzerland.
Lane JM, FL Ruben, JM Neff, JD Millar. Complications of smallpox vaccination. The New England Journal of Medicine. 1969; vol. 281, No. 22: pp. 1201-1208, copyright by the Massachusetts Medical Society.
Wharton M, RA Strikas, R Harpaz, LD Rotz, B Schwartz, CG Casey et al. Recommendation for using smallpox vaccine in a pre-event vaccination program. Supplemental recommendations of the Advisory Committee on Immunization Practices (ACIP) and the Health care Infection Control Practices Advisory Committee (HICPAC). MMWR Recommendation Report 2003;52(RR-7): 1-16.
Cono J, CG Casey, DM Bell. Smallpox vaccination sand adverse reaxtions. Guidace for clinicians. MMWR Recommendation Report 2003; 52(RR-4):I-28.
Xiong X, JL Smith, MS Chen. Effect of incorporation of cidofovir into DNA by human cytomegalovirus DNA polymerase on DNA elongation. Antimicrobial Agents and Chemotherapy. 1997; vol. 41, No. 3: pp. 594-599, copyright by American Society for Microbiology.

(Continued)

Primary Examiner — Stacy B. Chen
(74) Attorney, Agent, or Firm — Mark E. Stallion, Esq.; Husch Blackwell LLP (57) ABSTRACT

The invention provides kits, methods and compositions of matter which improve the safety of vaccination. By combining the administration of antiviral drugs, particularly ester derivatives of cidofovir, with the administration of viral vaccines, particularly the variola vaccine DryVax, side effects of the vaccine are diminished without significantly affecting the effectiveness of the vaccine.

5 Claims, 5 Drawing Sheets

(56) References Cited

OTHER PUBLICATIONS

Bowersock TL, S Martin. Vaccine delivery to animals. Advance in Drug Delivery Reviews. 1999; vol. 38: pp. 167-194, copyright by Elsevier Science B.V.

Buller, R.M.L., Owens, G., Schriewer, J., Melman, L., Beadle, J., and Hostetler, K.Y. 2004. Efficacy of oral active ether lipid analogs of cidofovir in a lethal mousepox model. Virology. vol. 318: pp. 474-481, copyright by Elsevier Inc.

Hood EE, DR Witcher, S Maddock. Commerial production of avidin from transgenic maize: characterization of transformant, production, processing, extraction and purification. Molecular Breeding. 1997; vol. 3: pp. 291-306, copyright by Kluwer Academic Publishers, Belgium.

Nally JE, S Artishin, AS Shoeran. Induction of mucosal and systemic antibody specific for SeMF3of streptococcus equi byintranasal vaccination using a sucrose acetate isobutyrate based delivery system. Vaccine. 2000; vol. 19: pp. 492-497, copyright by Elsevier Science Ltd.

Singh M, Briones M, O'Hagan, DT. A novel bioadhesive intranasal delivery system for inactivated influenza vaccines. Journal of Controlled Release. 2001; vol. 70: pp. 267-276, copyright by Elsevier Science B.V.

Opdebeeck JP, Tucker IG. A cholesterol implant used as delivery system to immunize mice with bovine serum albumin. Journal of Controlled Release. 1993; 23: pp. 271-279, copyright by Elsevier Science Publishers B.V.

Ulmer JB, Donnelly JJ, Parker SE, et al. Heterologous protection against influenza by injection of DNA encoding a viral protein. Science. Mar. 19, 1993;vol. 259: pp. 1745-1749, copyright by the American Association for the Advancement of Science.

Cox GJM, Zamb TJ, Babiuk LA. Bovine herpesvirus 1: immune responses in mice and cattle infected with plasmid DNA. Journal of Virology. 1993; vol. 67, No. 9: pp. 5664-5667, copyright by American Society for Microbiology.

Chen SC, Jones DH, Fynan EF, et al. Protective immunity induced by oral immunization with a rotavirus DNA vaccine encapsulated in microparticles. Journal of Virology. 1998; vol. 72, No. 7: pp. 5757-5761, copyright by American Society for Microbiology.

Moldoveanu Z, M Novak, WQ Huang, RM Gilley, JK Staas, D Schafer, RW Compans, J Mesecky. Oral immunization with influenza virus in biodegradable microspheres. The Journal of Infectious Diseases. 1993; vol. 167: pp. 84-90, copyright by The University of Chicago.

Fenner, et al., Smallpox and Its Eradication, Chapter 7, 1988, WHO.

* cited by examiner

Responses of A/NCr Mice Vaccinated in the Presence or Absence of Cidofivir to Increasing Doses of Ectromelia Virus

| cidofovir | + | − | + | − | + | − | + | − | + | − |
|---|---|---|---|---|---|---|---|---|---|---|
| vaccine | + | + | + | + | + | + | + | + | + | − |
| challenge dose (pfu/mouse) | 2.50E+04 | | 1.90E+03 | | 2.50E+02 | | 1.26E+01 | | | |

METHODS AND COMPOSITIONS FOR VACCINATION

CROSS-REFERENCE TO RELATED APPLICATIONS

This application is a national stage filing under 35 U.S.C. §371 from the international patent application PCT/US2005/018682 having an international filing date of May 26, 2005 that claims priority to and the benefit of U.S. Provisional Patent application No. 60/576,840 filed on Jun. 3, 2004 which documents are hereby incorporated by reference to the extent permitted by law.

GOVERNMENT SUPPORT CLAUSE

This invention was made with government support under Grant No. N01-AI-15436 awarded by The U.S. NIH/NIAD. The government has certain rights in the invention.

BACKGROUND OF THE INVENTION

1. Field of the Invention

The present invention relates generally to vaccine compositions and methods of vaccination. Specifically, the invention relates to drug and vaccine combinations, which result in a decrease in the side effects of the vaccination while not affecting the efficacy of the vaccine. This discovery results in the increased safety of DNA viral vaccinations.

2. Summary of the Related Art

Vaccines

The global interest in alternative methods for controlling infectious diseases is largely responsible for the intensive efforts to create safe and effective vaccines. An ideal vaccine would have minimal adverse side effects, ideally only one injection would be required for desired efficacy, the vaccine would have a reasonable duration of immunity, the cost of the product will be economically feasible and the vaccine must be relatively easy to produce.

There are many types of vaccines, including inactivated, live attenuated combined vaccines, vector combined vaccines such as viral vectors and bacterial vectors, microencapsulated combined vaccines, naked DNA combined vaccines and synthetic polypeptide combined vaccines. Inactivated vaccines contain entire pathogenic microorganisms that are inactivated by heat or chemical methods to insure that they are not capable of replication in the vaccinated animal while retaining their ability to induce a protective immune response. The primary advantage to this form of vaccine is that it does not require prior identification of the antigenic epitopes or molecules, which cause a microorganism to be pathogenic, since the entire microorganism is included in the vaccine preparation. This type of vaccine is safe, simple, and generally inexpensive to produce (Andre, 1994). In live attenuated combined vaccines the pathogenic microorganisms have been modified to diminish or eliminate the ability to cause disease (attenuated) while retaining the ability to replicate and induce protective immunity. The advantages to this type of vaccine over the inactivated forms are that they may elicit broader immune responses, require fewer doses, and generally induce longer-lasting protection.

Vector combined vaccines consist of live attenuated organisms that are either viral or bacterial, into which DNA, which encodes immunity-inducing antigens of pathogens, is inserted. A successful recombinant vector is capable of expressing one or more foreign genes, is infective after insertion of foreign DNA, and is inexpensive to produce and easy to administer. Examples of viral vectors include vaccinia, canarypox virus and adenovirus (Andre, 1994). As opposed to viral vectors, bacterial vectors have the advantage in that they are capable of being controlled by a variety of antibiotics. Bacterial vectors include *Vibrio cholera, Escherichia coli* and *Salmonella typhimurium* (Chatfield, 1994).

Microencapsulated combined vectors consist of antigens that are encapsulated in biodegradable microspheres, which protect the antigens against deleterious external influences. The release of antigens can be controlled by having particles (spheres) of different sizes. Furthermore, this presentation of antigen has an adjuvant effect on the immune response to the encapsulated antigens. Microcapsules can be given parenterally or orally (Anguado, 1992; Moldoveanu, 1993).

Naked DNA combined vaccines are based upon the transfection of DNA into a host without any carrier vector. Using recombinant DNA techniques, it is possible to insert a foreign gene into a plasmid to generate a recombinant plasmid. When the foreign gene is correctly inserted downstream of a useful promoter, an antigenic protein can be generated. In addition to their ability to induce both humoral and cell mediated immune responses, DNA vaccines have several other advantages over traditional vaccines. Many microbial proteins have folded structures that are altered during purification. If the shape of the recombinant protein is different from that of the native protein of the pathogen, antibodies induced by the recombinant protein will not recognize the native protein of the pathogen leading to vaccine failure. In case of DNA vaccination, since the pathogenic protein is synthesized in its native form inside the host cell, the chances of vaccine failure due to the incorrect protein folding are minimal. In addition, DNA vaccines are non-infectious, economical to produce in large amounts, and easy to purify using simple and inexpensive procedures (Weiner, 1999; Gurunathan, 2000).

Nucleic acids are also being investigated as a method of immunization, where DNA is injected into the muscle or skin of a mammal, which subsequently produces the antigen encoded by the administered DNA (Ulmer, 1993). The nucleic acid encoded a bovine herpes virus glycoprotein gD has been shown to induce a neutralizing immune response upon injection into cattle (Cox, 1993). Nucleic acids can be administered by a variety of routes in addition to injection into muscle or skin, including transcutaneously and orally (Chen, 1998).

Progress in determining the genomic sequence of a pathogen, together with technology enabling the synthesis of polypeptides have allowed for the construction of combination vaccines that bear the immunity inducing epitopes of many different antigens. For example, a pure polysaccharide vaccine against pneumococcal disease, which contains 23 different antigenic components and is referred to as a 23-valent vaccine (Fedson, 1999), has been successfully employed.

New vaccine manufacturing and delivery technology is continuously coming online. For example, high amounts of stable vaccine antigens can now be expressed in plants such as corn, the primary diet for livestock (Hood, 1998). While a variety of one-shot injectable conventional vaccines exist on the market today, many of these products are not as effective as two injections of the same vaccine. Consequently, several methods are currently under investigation for more sustained delivery of antigen, including sustained release gel such as poly lactide co-glycolide encapsulation (Atrigel®(Bowerstock, 1999) and Saiber™ (Nally, 2000)). Microparticles have also been used to target antigens with adjuvants to adhere to nasal mucosa (Singh, 2001). Solid implants have also been studied as a mechanism for long-lasting antigen release over time (Opdebeeck, 1993).

Antiviral Agents

Antiviral agents are generally modeled to inhibit viral replication within an infected cell. Effective antiviral agents specifically target steps within the viral replication pathway, thereby inhibiting or hindering viral replication within infected host cells while having a minimal cytotoxic effect on the host.

Two types of antiviral agent are alpha and beta interferons. The interferons are cytokines, which are secreted by virus infected cells. They bind to specific receptors on adjacent cells and protect them from infection by viruses. In addition to these direct antiviral effects, alpha and beta interferon also enhance the expression of class I and class II MHC molecules on the surface of infected cells, and thereby enhance the presentation of viral antigens to specific immune cells. Their presence can be demonstrated in body fluids during the acute phase of virus infection.

Protease inhibitors are another category of antiviral agents. The protease enzyme cleaves polyproteins of the virus into essential functional protein products during the maturation process of the virion. Protease inhibitors inhibit the function of the native protease enzyme, causing the virus to fail to mature and infect a new cell.

Another type of antiviral agent is nucleoside analogs. These analogs are synthetic compounds which resemble nucleosides, but have an incomplete or abnormal deoxy-ribose/or ribose group. These compounds are phosphorylated to the triphosphate form within the infected cell. In this form, the drug competes with normal nucleotides for incorporation into viral DNA or RNA. Incorporation into the growing nucleic acid chain results in irreversible association with the viral polymerase and consequent chain termination.

Cidofovir, known by the brand name Vistide®, is an acyclic nucleoside analogue of cytosine that upon incorporation into the host cell acts as a competitive inhibitor and alternate substrate for DNA polymerase. It is by this mechanism that Cidofovir inhibits DNA polymerase for most DNA viruses (Xiong X, 1997). Additionally in human papillomavirus, cidofovir induces DNA fragmentation and caspace-3e protease activity, thus inducing apoptosis in viral infected cells (Johnson JA, 1999).

While cidofovir was originally manufactured by Gilead Sciences to help combat cytomegalovirus retinitis in AIDS patient, it has antiviral activity against a broad range of DNA viruses including herpes-, adeno-, polyoma-, papilloma- and poxvirus (DeClercq E, 1997). Among the poxviruses, vaccinia, variola, cowpox, monkeypox, camelpox, molluscum contagiosum and orf have proven to be sensitive to the inhibitory effects of cidofovir (DeClercq, 2002). In vivo, cidofovir has shown high efficacy in protecting mice from a lethal dose of vaccinia, ectromelia or cowpox (DeClercq, 2002; Buller et al, 2004).

However, in order for cidofovir to be effective, it has to be administered via intravenous (i.v.) or subcutaneous injection, as its oral bioavailability is low. While the cytotoxicity of the CDV analogs is higher than that of cidofovir in vitro, the effective concentration to cause 50% plaque reduction is >100 fold lower for the cidofovir analogs giving a significantly higher selective index.

Cyclic nucleoside analogs upon esterification have been shown to have improved pharmacokinetic or pharmacodynamic properties (U.S. Pat. No. 5,886,179, which is incorporated herein by reference). Furthermore nucleoside analog esters are reported to have reduced toxicity as compared with the parent analog (U.S. Pat. No. 5,886,179). Cidofovir is potent when administered parentally or by aerosol but is not well absorbed orally. Esterification of cidofovir with two long chain alkoxyalkanols 3-hexadecyloxy-1-propanol (HDP-CDV) or 3-octadecyloxy-1-ethanol (ODE-CDV) increases the oral activity of cidofovir (Kern, 2002). However esterified cidofovir was also shown to have increased toxicity related to cidofovir in human foreskin fibroblast cells that were infected with vaccinia virus or cowpox virus (Kern, 2002).

Small Pox Vaccination

Non-esterified cidofovir is currently for treatment of the side effects of smallpox vaccination. Smallpox vaccination was routinely given to U.S. children until 1972 (Henderson et al, 1999). In 1980 the World Health Organization declared that smallpox had been eradicated worldwide (World Health Organization report, 1980). Due to concerns of smallpox use as a biological weapon, the U.S. government has restarted smallpox vaccination. The only smallpox vaccine licensed in the United States is Dryvax (Wyeth Laboratories Incorporated, Marietta, Pa.) which is a dried calf lymph type vaccine. However there can be adverse reactions to the vaccine itself. One thousand of every one million vaccines will have a serious reaction to the vaccine and one in every million vaccines will die (Lene et al, 1969). Serious reactions to the vaccine include autoinoculation, central nervous system disease, progressive vaccinia and generalized vaccinia. Vaccinia immune globulin can be used to treat patients with extensive autoinoculation, progressive vaccinia and severe or recurring generalized vaccinia (Wharton et al, 2003). Vaccinia immune globulin is a product made from the blood plasma of recently vaccinated people, which is high in antibodies against vaccinia.

Cidofovir is an investigation drug protocol that has in vivo and in vitro activity against vaccinia virus (Cono J et al, 2003). Thus far cidofovir has not been used to treat vaccinia virus infections in humans and is reserved for treatment of patients who do not respond to vaccinia immune globulin or are near death (Cono J et al, 2003).

REFERENCES

The following references are cited throughout the application and are herein incorporated by reference. The applicant reserves the right to challenge the veracity of any of these references.

Henderson D A, T V Inglesby, J G Bartlett, M S Ascher, E Eitzen, P B Jahrling et al. Smallpox as a biological weapon: medical and public health management. Working Group on Civilian Biodefense. JAMA 1999; 281:2127-37.

Johnson J A, J D Gangemi. Selective inhibition of human papillomavirus induced cell proliferation by (S)-1-[3-hydroxy-2-(phosphonylmethoxy)propyl]cytosine. Antimicrob Agents Chemother. 1999; 43(5): 1198-205.

World Health Organization. The global eradication of smallpox: final report of the Global Commission for the Certification of Smallpox Eradication, Geneva, December 1979. Geneva: World Health Organization, 1980.

Lene J M, F L Ruben, J M Neff, J D Millar. Complications of smallpox vaccination. N Engl J Med 1969; 281:1201-8.

Wharton M, R A Strikas, R Harpaz, L D Rotz, B Schwartz, C G Casey et al. Recommendation for using smallpox vaccine in a pre event vaccination program. Supplemental recommendations of the Advisory Committee on Immunization Practices (ACIP) and the Health care Infection Control Practices Advisory Committee (HICPAC). MMWR Recommendation Report 2003; 52(RR-7): 1-16.

Cono J, C G Casey, D M Bell. Smallpox vaccination sand adverse reaxtions. Guidance for clinicians. MMWR Recommendation Report 2003; 52(RR-4): 1-28.

DeClercq E. Therapeutic potential of Cidofovir (BPMPC, Vistide) for the treatment of DNA virus (i.e. herpes-, papova-, pox- and adnovirus) infections. Verh K Acad Geneeskd Belt 1996; 58(1):19-47.

Xiong X, J L Smith, M S Chen. Effect of incorporation of cidofovir into DNA by human cytomegalovirus DNA polymerase on DNA elongation. Antimicrob Agents Chemother. 1997; 41(3):594-9.

U.S. Pat. No. 5,886,179

Bowersock T L, S Martin. Vaccine delivery to animals. Advance in Drug Delivery Review. 1999; 38:167-194.

Buller, R. M. L., Owens, G., Schriewer, J., Melman, L., Beadle, J., and Hostetler, K. Y. 2004. Efficacy of oral active ether lipid analogs of cidofovir in a lethal mousepox model. Virology 318: 474-481.

Hood E E, D R Witcher, S Maddock. Commercial production of avidin from transgenic maize: characterization of transformant, production, processing, extraction and purification. Molecular Breeding. 1998; 4:301-312.

Nally J E, S Artishin, A S Shoeran. Induction of mucosal and systemic antibody specific for SeMF3 of *streptococcus equi* by intranasal vaccination using a sucrose acetate isobutyrate based delivery system. Vaccine. 2000; 19:492-497.

Singh M, Briones M, O'Hagan, D T. A novel bioadhesive intranasal delivery system for inactivated influenza vaccines. J Control Release. 2001; 70:267-276.

Opdebeeck J P, Tucker I G. A cholesterol implant used as delivery system to immunize mice with bovine serum albumin. J Control Release. 1993; 23: 271-279.

Ulmer J B, Donnelly J J, Parker S E, et al. Heterologous protection against influenza by injection of DNA encoding a viral protein. Science. 1993; 259:1745-1749.

Cox G J M, Zamb T J, Babiuk L A. Bovine herpesvirus 1: immune responses in mice and cattle infected with plasmid DNA. J. Virol. 1993; 67:5664-5667.

Chen S C, Jones D H, Fynan E F, et al. Protective immunity induced by oral immunization with a rotavirus DNA vaccine encapsulated in microparticles. J. Virol. 1998; 72:5757-5761.

Aguado M T, P H Lamber. Controlled release vaccines-biodegradable polylactide/polyglycolide microspheres as antigen vehicles. Immunobiology. 1984; 113-125.

Moldoveanu Z, M Novak, W Q Huang, R M Gilley, J K Staas, D Schafer, R W Compans, J Mesecky. Oral immunization with influenza virus in biodegradable microspheres. J Infect Diseases. 1993; 16:84-90.

Weiner D B, R C Kennedy. Genetic Vaccines. Scientific American, 1999.

Gurunathan S, D M Klinman, R A Seder. DNA vaccines: Immunology, Application and Optimization, Ann. Rev. Immunol. 2000; 18:927-974.

Fedson D, Musher D, Eskola J. Pneumococcal vaccine. In: Vaccines, 3rd ed. Plotkin S, Orenstein W, editors. Philadelphia: WB Saunders Company; 1999.

Andre F E, W J Stanbury, D E Teuwen. Conventional and New Generation Combined Vaccines. In: Modern Vaccinology. Kurstak E, editor. New York: Plenum Publishing Corporation; 1994.

Chatfield S N, G Dougan, M Roberts. Progress in the Development of Multivalent Oral Vaccines Based on Live Attenuated *Salmonella*. In: Modern Vaccinology. Kurstak E, editor. New York: Plenum Publishing Corporation; 1994.

SUMMARY OF INVENTION

The inventor has made the surprising discovery that administering cidofovir, or analogs thereof, with a smallpox vaccine, preferably Dryvax, resulted in a decrease in the side effects of vaccination without affecting the efficacy of the vaccination. Based upon that discovery, the inventor envisions the co-administration of any antiviral agent with any live vaccine will decrease the side effects of the vaccination while maintaining or improving the efficacy of the vaccine.

Thus in one embodiment the invention is drawn to a method of vaccinating a mammal including but not limited to humans, mice, rats, companion animals and livestock, comprising the steps of administering an antiviral agent and administering a vaccine to the mammal.

The antiviral agent and the vaccine may be administered as an admixture in a single composition, or as separate compositions. Administration of separate compositions is particularly preferred when the desired mode of administering the antiviral agent and vaccine differ, or when the carrier for the antiviral agent and the carrier for the vaccine differ. The antiviral agent and the vaccine may administered separately but concurrently, or separately but substantially concurrently, at appropriate dosage levels. The separate compositions may be administered sequentially in any order. For example, treatment with the agent may occur on day 1 and the vaccine on day 2, or vice versa. The exact regiment will depend on one or several factors, such as the virus being vaccinated against.

Preferably, the antiviral agent is a nucleoside analog, more preferably cidofovir, most preferably an esterified derivative of cidofovir. Preferred viruses to which the vaccine is directed are Influenza, Rabies, Mumps, Polio, Hepatitis A, Hepatitis B, HIV/AIDS and most preferred is Smallpox virus, variola.

The antiviral agent may be administered before, during or after the actual vaccine. Alternatively, the antiviral agent may be mixed with the vaccine prior to administration. Preferred vaccine is a live virus or a nucleic acid capable of replication.

In another embodiment, the invention is drawn to a pharmaceutical composition comprising an antiviral agent and a vaccine wherein the antiviral agent reduces a side effect of the vaccine while maintaining or improving the efficacy of the vaccine.

In yet another embodiment, the invention is drawn to a kit comprising an antiviral agent and a vaccine. Such kits may further include, if desired, one or more of various conventional pharmaceutical kit components, such as, for example, containers with one or more pharmaceutically acceptable carriers, as would be readily apparent to those skilled in the art. Printed instructions, such as inserts or as labels, indicating quantities of the components to be administered, guidelines for administration and/or guidelines for mixing the components, may also be included in the kit. Preferred antiviral agents include antisense oligonucleotides, binding and fusion inhibitors, glucosidase inhibitors, immunomodulators, inhibitors of hepatitis B virus, inhibitors of respiratory viruses, nucleoside analog inhibitors of herpesvirus, non-nucleoside inhibitors of herpesvirus, non-nucleoside reverse transcriptase inhibitors, nucleoside analog inhibitors of HIV, protease inhibitors, ribonucleotide reductase inhibitors. Preferred vaccines include, Daptacel, Flumist, Flu Shield, flu Virin, Havrix, Im0 Vax, Infanrix, Ipol, Meningitec, Menjugate, Meruvax II, M-R Vax, MMR, Mumpsvax, Orimune, Pavivac, Pediarix, Pentacel, Prevnar, Quadracel, Rabies Vaccine, REcombivax, Salk, Sabin, Sci-B-Vax, Salk, Tripedia, Varivax, Vaxgen, Dryvax and the new smallpox vaccine ACAM 2000.

BRIEF DESCRIPTIONS OF THE DRAWINGS

FIG. 5. Time course of lesion resolution. A/NCR mice were treated with 12.5 mg/kg CDV on days 0, 1, 2, 3, and 4 or HDP-CDV 10 mg/kg on day 0 and 4 mg/kg on days 1, 2, 3, and 4 following vaccination on day 0. Lesions were scored blind on a 4 point scale and plotted as averaged against the day post inoculation. Standard errors not shown but all fall within 10% of the values of the group.

DETAILED DESCRIPTION OF THE INVENTION

The instant invention is based upon the discovery of an effective and safe vaccination combination, comprising an antiviral agent and a vaccine. An important aspect of the invention is the decrease in side effects of the vaccination when administered with the antiviral agent. Therefore the invention is drawn to methods of vaccinating, comprising administering an antiviral agent and vaccine; compositions comprising an antiviral agent and a vaccine; and kits comprising an antiviral agent and vaccine.

The skilled artisan would readily recognize how to administer a vaccine, which may be, but not limited to, an injectable liquid; a consumable transgenic plant that expresses the vaccine, antiviral agent, or combination thereof; a sustained release gel or an implantable encapsulated composition; a solid implant; or a nucleic acid. The vaccine or antiviral agent may also be administered in a cream, lotion, ointment, skin patch, lozenge, or oral liquid such as a suspension, solution and emulsion (oil in water or water in oil).

Pharmaceutical compositions of the present invention may be in any form suitable for administration. Such administrable forms include tablets; buffered tablets; pills; capsules; enteric-coated capsules; powders; granules; aerosols; liposomes; creams; lotions; ointments; skin patches; lozenges; oral liquids such as suspensions, solutions and emulsions (oil in water or water in oil); or injectable liquids.

In one embodiment of the present invention, the antiviral agent and vaccine are administered in one composition.

Thus, a composition comprising an antiviral agent is prepared by admixture of the analog with at least one suitable pharmaceutically acceptable carrier to achieve an antiviral agent composition in the desired administrable form. Likewise, a composition comprising a vaccine is prepared by admixture with at least one suitable pharmaceutically acceptable carrier to achieve a composition in the desired administrable form. The antiviral agent and the vaccine may be administered together as an admixture, administered separately but currently or separately but substantially concurrently, at appropriate dosage levels.

In another embodiment, the antiviral agent and the vaccine are administered as separate compositions, which is particularly preferred when the desired mode of administering the antiviral agent and vaccine differ. The combination can be administered sequentially, that is treatment with either the antiviral agent first and the vaccine second, or vice versa; or the combination can be administration at the same time. For example, treatment with the antiviral agent may occur on day 1 and the vaccine on day 2, or vice versa. The exact regiment will depend on the virus being vaccinated against.

A pharmaceutical combination in kit form may be provided which includes in packaged combination an antiviral agent composition and a vaccine composition, which may be in different or same administrable forms. For example, the antiviral agent composition may be in an orally administrable form such as a tablet, pill, capsule or powder, whereas the vaccine may be in a form suitable for administration by injection, such as in solution form. Such kits may further include one or more various conventional pharmaceutical kit components, such as, for example, containers with one or more pharmaceutically acceptable carriers and additional containers, as will be readily apparent to those skilled in the art. Printed instructions, such as inserts or as labels, indicating quantities of the components to be administered, guidelines for administration and/or guidelines for mixing the components, may also be included in the kit.

Definitions

As used herein, the term "therapeutically effective amount" refers to the quantity of a compound which is sufficient to yield a desired therapeutic response without undue adverse side effects (such as toxicity and allergic response) commensurate with a reasonable benefit/risk ratio when used in the manner of the invention As used herein, the term "pharmaceutical carrier" is a pharmaceutically acceptable solvent, suspending agent or vehicle for delivering the nucleoside derivative or vaccine to the animal or human. The carrier can be liquid or solid and is selected with the planned manner of administration in mind.

Included within the term "nucleoside analog" as used herein, is the nucleoside derivative thereof, i.e., the mono, di or triphosphate derivative. Examples of nucleoside analogs include cidofovir (vistide), adefovir (preveon) and the oral prodrug form of PMPA, known as bis-POC-PMPA.

As used herein, the term "antiviral agent" refers to an agent which inhibits or stops the growth and reproduction of viruses. This action may occur either by direct action on the virus or indirectly by acting on the cells of the body. Antiviral agents include protease inhibitors and nucleotide polymerase inhibitors. Table 1 provides a non-limiting list of soemantiviral agents.

TABLE 1

| Antiviral Agents | |
|---|---|
| Category of Antiviral Agent | Specific Drug Names |
| Antisense oligonucleotides | AR177 |
| | fomivirsen sodium |
| | GEM 132 |
| | GEM 91 |
| | GEM 92 |

TABLE 1-continued

Antiviral Agents

| Category of Antiviral Agent | Specific Drug Names |
|---|---|
| Binding and fusion inhibitors: HIV | AMD 3100 |
| | n-docosanol |
| | PRO2000 |
| | T-1249 |
| | T-20 |
| Binding and fusion inhibitors: Non-HIV | arbidol |
| | n-docosanol |
| | SP-303 |
| Cellular targets | hypericin |
| Glucosidase inhibitors | MDL 28574 |
| | SC-48334 |
| Immunomodulators | ADA |
| | imiquimod |
| | ISIS 5320 |
| | resiquimod |
| Inhibitors of hepatitis B virus | adefovir dipivoxil |
| | DAPD |
| | emtricitabine |
| | entecavir |
| | lamivudine |
| Inhibitors of respiratory viruses | amantadine |
| | oseltamivir |
| | pirodavir |
| | pleconaril |
| | ribavirin |
| | rimantadine |
| | WIN 54954 |
| | zanamivir |
| Non-nucleoside inhibitors of herpesviruses | foscarnet |
| | maribavir |
| Non-nucleoside RT inhibitors (NNRTI) of HIV | ABT-378 |
| | atevirdine mesylate |
| | calanolide A |
| | capravirine |
| | efavirenz |
| | emivirine |
| | GW420 867X (aka HBY 1293) |
| | HBY 097 |
| | L-697,661 |
| | loviride |
| | MIV-150 |
| | nevirapine |
| | PETT-5 |
| | R165335-TMC125 |
| | talviraline |
| | tivirapine |
| | trovirdine |
| Nucleoside analogue inhibitors of herpesviruses | acyclovir |
| | brivudin |
| | cidofovir |
| | cyclic HPMPC |
| | famciclovir |
| | fiacitabine |
| | fialuridine |
| | ganciclovir |
| | GW-273175X |
| | idoxuridine |
| | lobucavir |
| | netivudine |
| | penciclovir |
| | sorivudine |
| | trifluridine |
| | valaciclovir |
| | valomaciclovir stearate |
| | vidarabine |
| Nucleoside analogues inhibitors of HIV (NRTI) | 935U83 |
| | abacavir |
| | adefovir |
| | adefovir dipivoxil |
| | alovudine |
| | AZdU |
| | CS-92 |
| | DAPD |
| | didanosine |
| | dOTC |
| | emtricitabine |
| | fozivudine tidoxil |
| | lamivudine |
| | lobucavir |
| | lodenosine |
| | stavudine |
| | tenofovir |
| | tenofovir disoproxil fumarate |
| | zalcitabine |
| | zidovudine |
| Protease inhibitors | A-77003 |
| | AG7088 |
| | amprenavir |
| | BMS-232632 |
| | delavirdine |
| | DMP-323 |
| | DMP-450 |
| | GW 433 908 |
| | indinavir |
| | KNI-272 |
| | lasinavir |
| | lopinavir |
| | Mozenavir |
| | nelfinavir |
| | PD178390 |
| | ritonavir |
| | RPI 312 |
| | saquinavir |
| | SC-52151 |
| | SDZ PRI 053 |
| | tipranavir |
| | U-103017 |
| | U-96988 |
| Ribonucleotide reductase inhibitors | Hydroxyurea |
| Unknown - selectively kills HIV-infected cells | AGI549 |
| | foscarnet |
| | LiGLA |

As used herein, the term "antiviral activity" refers to the ability of an agent to inhibit or hinder viral replication within infected host cells while preferably having a minimal cytotoxic effect on the host.

As used herein, the term "adjuvant" refers to a substance injected along with an antigen or vaccine to enhance the immune response stimulated by the antigen; also, drug or agent added to another drug or agent to enhance its medical effectiveness.

As used herein, the term "plaque forming unit" refers to a unit of infectious virus particles. The infectious virus particles are calculated by growing cells until they form a monolayer of cells. The cells are then infected with a virus and the liquid growth medium is replaced with a semi-solid one so that any virus particles produced as the result of an infection cannot move far from the site of their production. A plaque is produced when a virus particle infects a cell, replicates, and then kills that cell. This process may repeat several times. The cells are then stained with a dye which stains only living cells. The dead cells in the plaque do not stain and appear as unstained areas on a colored background. Each plaque is the result of infection of one cell by one virus followed by replication and spreading of that virus. (However viruses that do not kill cells may not produce plaques.)

As used herein, the term "naked DNA" refers to purified DNA, which may be injected into a mammal for the purpose of vaccination.

As used herein, the term "vaccine" is used to describe a substance which elicits an immune response or provides protective immunity. The terms vaccinate and immunize are used interchangeably. Table 2 provides a non-limiting list of vaccines that are currently available.

TABLE 2

Currently Marketed Vaccines

| Marketed Name | Diseases Vaccinate Against |
|---|---|
| Agrippal | Influenza Virus |
| Daptacel | Tetanus, Diphtheria and Whooping Cough |
| Dryvax | Smallpox |
| Flumist | Influenza Virus |
| Flu Shield | Influenza Virus |
| Flu Virin | Influenza Virus |
| Havrix | Hepatitis A |
| Im0 Vax | Rabies Vaccine Adsorbed |
| Infanrix | Diphtheria, Tetanus and Pertussis |
| Ipol | Polio |
| Meningitec | Meningitis C |
| Menjugate | Meningitis C |
| Meruvax II | Rubella Virus |
| M-R Vax | Measles and Rubella Virus |
| MMR | Measles Mumps Rubella |
| Mumpsvax | Mumps Virus |
| Orimune | Poliovirus |
| Pavivac | Mumps |
| Pediarix | Polio, Tetanus, Hepatitis B, Pertussis, Diphtheria |
| Pentacel | Polio, Tetanus, Haemophilus b, Pertussis, Diptheria |
| Prevnar | Pneumococcal |
| Quadracel | Diphtheria, Pertussis, Tetanus, Polio |
| Rabies Vaccine | Rabies |
| Recombivax | Hepatitis B |
| Salk | Polio |
| Sabin | Polio |
| Sci-B-Vac | Hepatitis B |
| Tripedia | Diphtheria, Tetanus, Pertussis |
| Varivax | Varicella Virus |
| Vaxgen | HIV/AIDS |

The following examples are provided to demonstrate preferred embodiments of the invention and are not meant to limit the invention. Those skilled in the art to which this invention is directed will, in light of the present disclosure, appreciate that changes can be made in the specific embodiments which are disclosed and still obtain a like or similar result without departing from the spirit and scope of the invention.

EXAMPLE 1

Mice were administered the Dryvax smallpox vaccine ($2.6 \times 10^4$, $9.0 \times 10^2$, $1 \times 10^2$, 100 and 0 plaque forming units (pfu) per ml) in the absence or presence of cidofovir. For five consecutive days including the day of challenge, mice were given an intraperitoneal dose of cidofovir. The mice were then challenged in a nose only inhalation system under a constant aerosol dose, giving each animal a presented dose of $\sim 2 \times 10^4$ pfu. For five consecutive days, including the day of the challenge, mice are given an intraperitoneal dose of cidofovir. Average antibody titers of surviving mice are stated above each bar in FIG. 1 for doses of $1.3 \times 10^6$ and $4.7 \times 10^5$ pfu/mouse.

Figure 1:
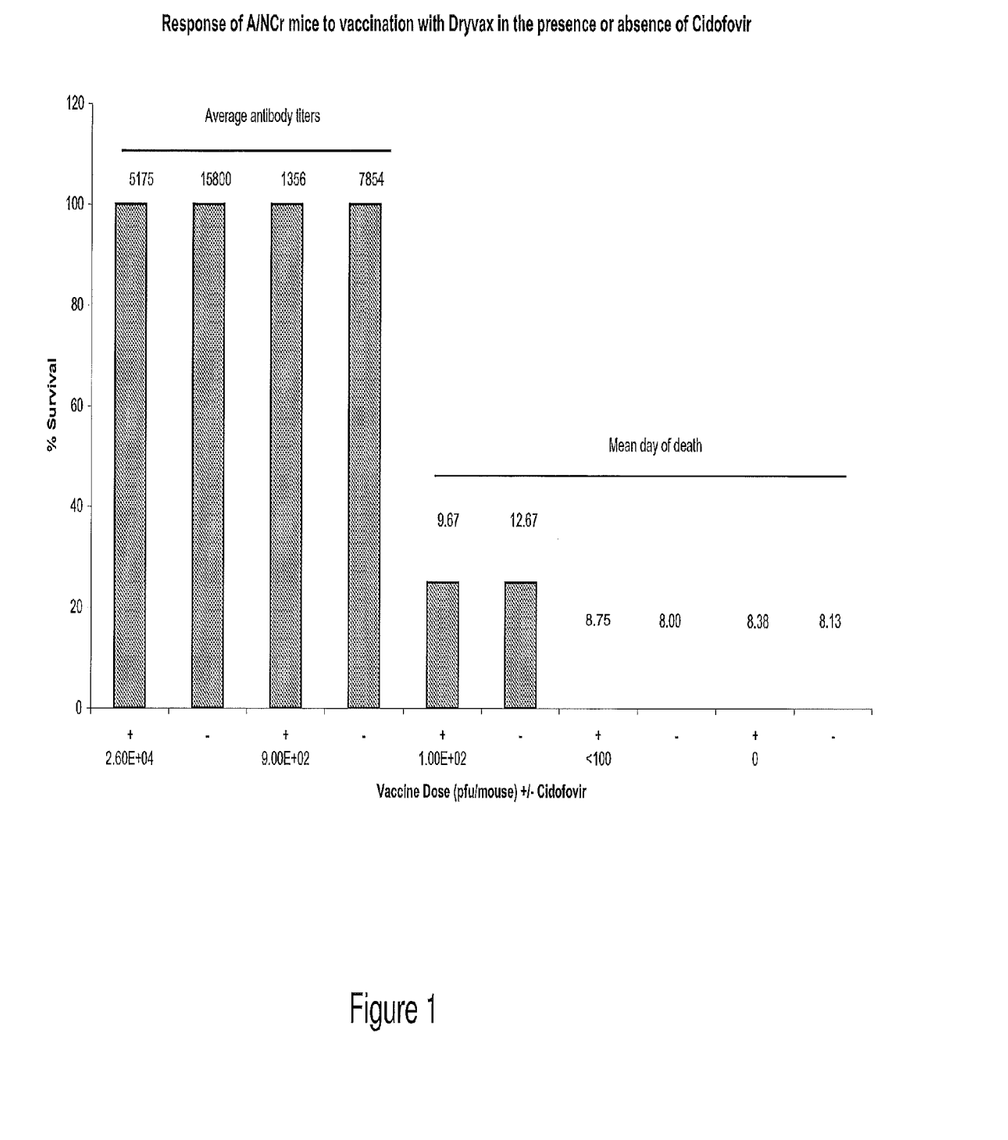
FIG. 1. The absence or presence of cidofovir during vaccination with decreasing doses of the dryvax smallpox vaccine did not significantly affect protection from aerosol challenge with ectromelia virus.

At $1.3 \times 10^6$ and $4.7 \times 10^5$ pfu/ml vaccine dose 100% of the mice survived in the absence and presence of cidofovir (see FIG. 1). The average antibody titers were greater than 1000. At $5 \times 10^4$ pfu/ml vaccine dose ~23% of the mice survived. The cidofovir did not affect the mortality rate. The absence of the vaccine (0 pfu/ml) and low vaccine dose (<1000 pfu/ml) resulted in 100% mortality.

This data show that the absence or presence of cidofovir during vaccination with decreasing doses of the dryvax smallpox vaccine did not significantly affect protection from aerosol challenge with ectromelia virus.

EXAMPLE 2

Figure 2:
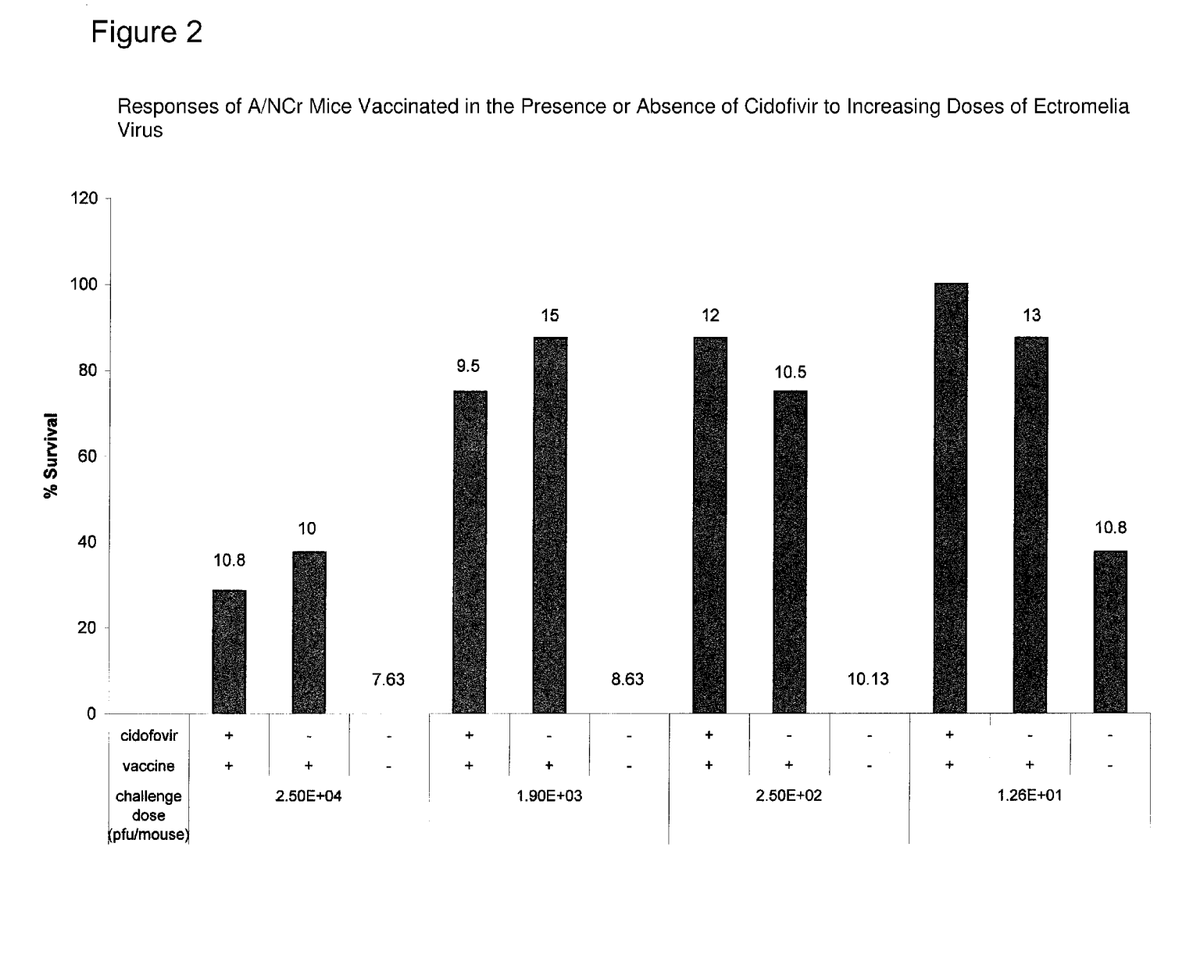
FIG. 2. The presence or absence of cidofovir during dryvax vaccination did not affect the level of protection from lethal disease following increasing doses of aerosolized ectromelia virus.

Mice were vaccinated with the DryVax smallpox vaccine $3.1 \times 10^4$ pfu/ml and subsequently treated with intraperitoneal injections of cidofovir (12.5 mg/kg/day×5 days). The animals were then challenged with an increasing dose of ectromelia virus ($2.5 \times 10^4$, $1.9 \times 10^3$, $2.5 \times 10^2$ and $1.2 \times 10^1$ pfu/mouse) (see FIG. 2). The presence or absence of cidofovir during DryVax vaccination did not affect the level of protection from lethal disease following increasing doses of aerosolized ectromelia virus.

EXAMPLE 3

The current smallpox vaccine is very reactive in humans. Standard vaccination is a percutaneous scarification of $\sim 2 \times 10^5$ pfu of live vaccinia virus (Dryvax). The resulting lesion can take up to 42 days to resolve. Treatments with the potential to hasten the resolution of lesion without affecting vaccine efficacy would be welcomed in the clinic. Vaccination in the presence of an antiviral limits the replication of the virus, leading to a smaller and more rapidly resolving lesion. The skilled artisan might reasonably expect that this approach may result in a reduction in the strength of the immune response due to a lower mass of viral antigen. Applicant tested this hypothesis using the antiviral Cidofovir (CDV) and its lipid analog HDP-CDV.

Cidofovir is an acyclic nucleoside phosphonate of cytosine monophosphate that inhibits viral replication by replacing dCTP causing chain termination or directly inhibiting polymerase activity. CDV shows a higher selectivity for the viral polymerase in DryVax (vaccinia) than that of the cellular polymerase making it an excellent candidate for an antiviral therapy against poxviruses. The limited bioavailability of CDV and its nephrotoxic effects led to the development of a lipid analog of CDV in order to increase its oral bio-availability (hexadecyloxypropyl-CDV, HDP-CDV). In this example, applicant shows that treatment with CDV or HDP-CDV results in smaller vaccination lesions that resolve more rapidly.

A/NCr mice were vaccinated at the base of the tail through percutaneous scarification with Dryvax. On days 0, 1, 2, 3, 4 with respect to vaccination, mice were treated with 12.5 mg/kg of CDV delivered via intraperitoneal injection. For HDP-CDV, mice were treated with 10 mg/kg on day 0 and 4 mg/kg on days 1,2,3,4 delivered via gavage. Lesion development was scored every two days for ulceration, inflammation, and resolution.

Figure 3:
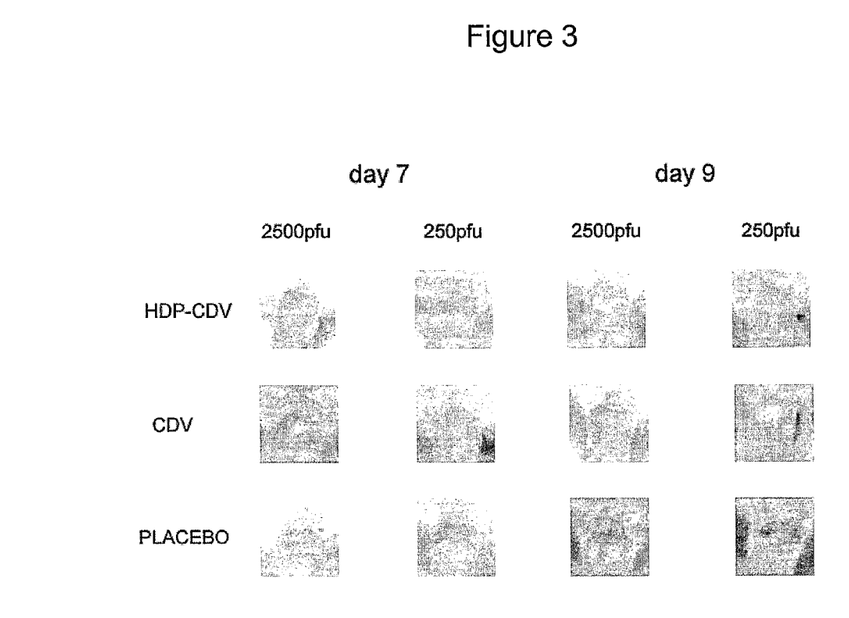
FIG. 3. Mice vaccinated in the presence of an antiviral show a decrease in lesion size and increased speed in lesion resolution. A/NCr mice were treated with either 12.5 mg/kg CDV on days 0, 1, 2, 3, and 4 or HDP-CDV 10 mg/kg on day 0 and 4 mg/kg on days 1, 2, 3, and 4 following vaccination on day 0. Mice were vaccinated with two doses of Dryvax and the lesions photographed every 2-3 days.
Figure 4:
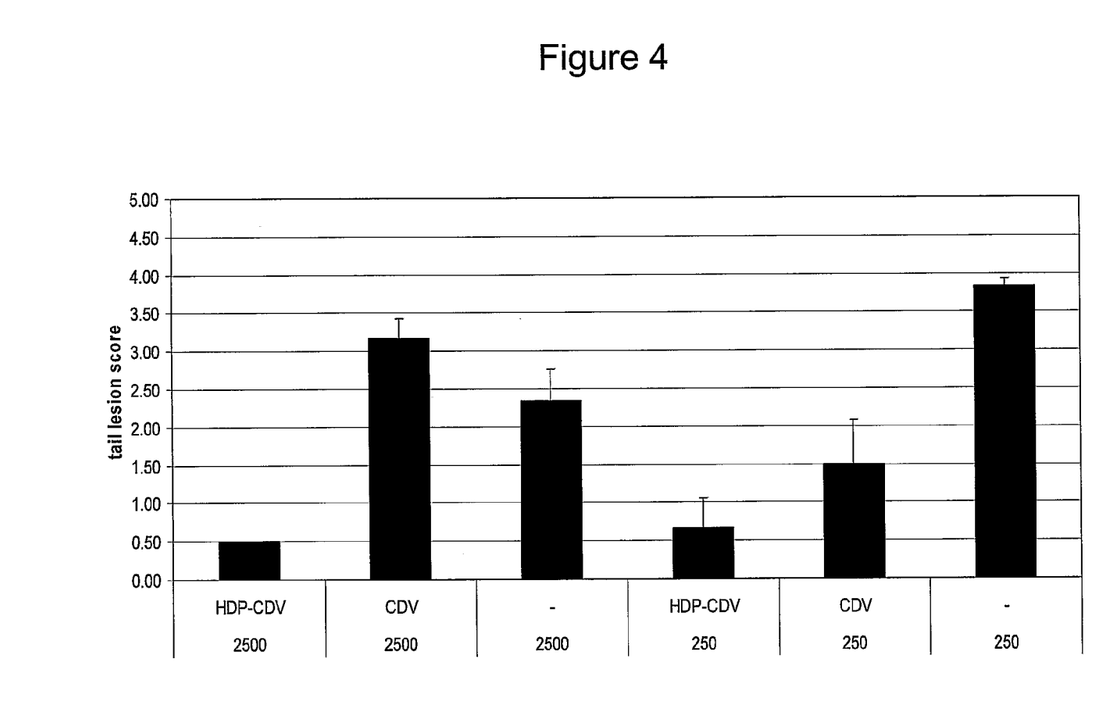
FIG. 4. Lesion development at 9 days following vaccination in the presence of HDP-CDV and CDV. A/NCr mice were treated with 12.5 mg/kg CDV on days 0, 1, 2, 3, and 4 or HDP-CDV 10 mg/kg on day 0 and 4 mg/kg on days 1, 2, 3, and 4 following vaccination on day 0. Mice were photographed on day 9 and scored blind. The scores were averaged with the standard error calculated for each group.
Figure 5:
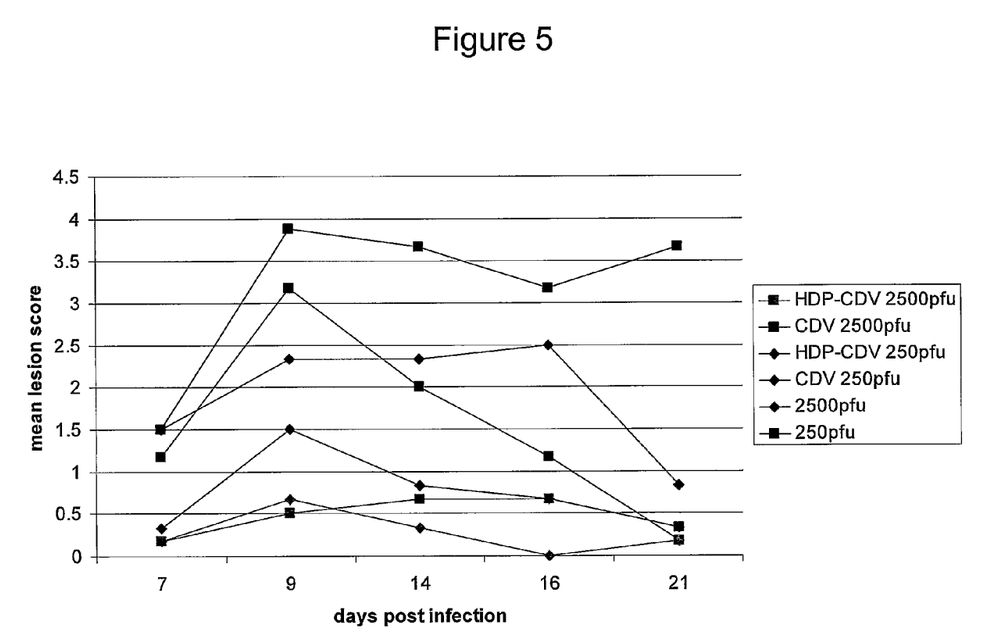

Lesion development was scored by erythema, edema, eschar formation, and resolution or healing on a graded point system. Every 2-3 days, the lesions were photographed. The photographed lesions were scored in a blinded fashion with the graded lesions averaged and the standard error calculated. FIG. 3 depicts a representative photo of the vaccination lesion from one mouse of each treatment group. FIG. 4 presents the mean tail lesion score for all mice in each treatment group at the peak of lesion development, 9 days post-vaccination. FIG. 5 displays lesion development and resolution over 21 days post-vaccination. Taken together this data show that HDP-CDV is more efficacious than CDV for attenuation of lesion development and acceleration of lesion resolution.

Applicant has demonstrated that the presence of CDV, and by inference HDP-CDV, during vaccination did not diminish vaccine protection against an aerosol challenge with a lethal dose of ectromelia (ECTV). Groups of mice were vaccinated with three sequential 10-fold dilutions of Dryvax vaccine in the presence or absence of CDV and then challenged with aerosol ECTV. There was no difference observed in protection from death afforded by vaccination in the presence or absence of CDV. The mice immunized at the two higher doses of vaccine in the presence of CDV showed lower pre-challenge anti-orthopoxvirus antibody titers, but the post challenge titers were similar.

Both CDV and HDP-CDV administered at the time of vaccination decreased the severity of vaccine lesions and facilitated healing. HDP-CDV appeared to be more efficacious than CDV in this process.

Cidofovir administered at the time of vaccination protected mice from a lethal ECTV aerosol challenge, and anti-orthopoxvirus antibody titers, which are a measure of effective immunity, showed similar levels post challenge regardless of the presence or absence of CDV during vaccination. Table 3 summarizes these results.

Table 3: A/NCr mice vaccinated in the presence of Cidofovir followed by lethal ECTV small particle aerosol challenge A/NCr mice were treated with CDV on days 0,1,2,3,4 following vaccination on day 0. Lesion scores were recorded on day 14. Antibody titers were performed on sera taken one day prior to and 21 days following challenge. Mice were challenged with ~2×10⁴ pfu aerosolized ECTV 21 days following vaccination.

| Dryvax ® dose (pfu/mouse) | Cidofovir treatment | Lesion score | % Survival | Pre-challenge titer | Post-challenge titer |
|---|---|---|---|---|---|
| 2.6 × 10³ | 12.5 mg/kg | 0 | 100 | 5175 | 198963 |
|  | 0 | 1-2 | 100 | 15800 | 70250 |
| 9.0 × 10² | 12.5 mg/kg | 0 | 100 | 1356 | 54500 |
|  | 0 | 0-1 | 100 | 7666 | 61000 |
| 1.0 × 10² | 12.5 mg/kg | 0 | 25 | 83 | 11000 |
|  | 0 | 0-1 | 25 | 1673 | 72000 |
| 0 | 12.5 mg/kg | 0 | 0 | <25 | N/A |
|  | 0 | 0 | 0 | <25 | N/A |

What is claimed is:

1. A method of vaccinating or immunizing an individual against smallpox virus comprising the steps of administering to an individual a nucleoside analog or a derivative of a nucleoside analog antiviral agent that is cidofovir or an analog of cidofovir and a vaccine or immunizing agent wherein the vaccine or immunizing agent elicits an immune response in the individual and the vaccine or immunizing agent is a live, attenuated smallpox vaccine, wherein the antiviral agent and the vaccine or immunizing agent are co-administered.

2. The method of claim 1, wherein the antiviral agent is selected from the group consisting of HDP-CDV and ODE-CDV.

3. A composition comprising a nucleoside analog or a derivative of a nucleoside analog antiviral agent that is cidofovir or an analog of cidofovir and a vaccine or immunizing agent against smallpox virus, wherein the vaccine or immunizing agent elicits an immune response in an individual and the vaccine or immunizing agent is a live, attenuated smallpox virus.

4. The composition of claim 3, wherein the immune response is selected from the group consisting of a humoral response, a cellular response, protective immunity, production of epitope specific antibody, and production of epitope specific T-cell.

5. The composition of claim 3, wherein the antiviral agent is selected from the group consisting of: HDP-CDV and ODE-CDV.

* * * * *

UNITED STATES PATENT AND TRADEMARK OFFICE
CERTIFICATE OF CORRECTION

PATENT NO.       : 8,541,167 B2
APPLICATION NO. : 11/569963
DATED            : September 24, 2013
INVENTOR(S)      : Robert Mark Buller It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1710 days.

Signed and Sealed this
Fifteenth Day of September, 2015

Michelle K. Lee
*Director of the United States Patent and Trademark Office*